United States Patent
Konstandin et al.

(10) Patent No.: US 8,033,381 B2
(45) Date of Patent: Oct. 11, 2011

(54) APPARATUS FOR SEPARATING PARTS

(75) Inventors: Horst Konstandin, Karlsbad (DE);
Mathias Herbach, Pfinztal (DE);
Jürgen Krazmeier, Bretten (DE);
Jörg-Uwe Bippus, Ettlingen (DE)

(73) Assignee: Romaco Pharmatechnik GmbH, Karlsruhe (DE)

( * ) Notice: Subject to any disclaimer, the term of this patent is extended or adjusted under 35 U.S.C. 154(b) by 8 days.

(21) Appl. No.: 12/653,211

(22) Filed: Dec. 10, 2009

(65) Prior Publication Data

US 2010/0158658 A1    Jun. 24, 2010

(30) Foreign Application Priority Data

Dec. 18, 2008 (DE) .......................... 10 2008 063 786

(51) Int. Cl.
*B65G 47/26* (2006.01)

(52) U.S. Cl. ...................... 198/458; 198/474.1; 198/456

(58) Field of Classification Search ............... 198/474.1, 198/471.1, 458, 456
See application file for complete search history.

(56) References Cited

U.S. PATENT DOCUMENTS

| | | | | |
|---|---|---|---|---|
| 3,446,161 A * | 5/1969 | Oddy | ............................ | 198/458 |
| 4,200,179 A | 4/1980 | Hinz | | |
| 4,913,170 A * | 4/1990 | Conti | ............................ | 198/458 |
| 5,070,994 A * | 12/1991 | Focke | ............................ | 198/458 |
| 6,068,317 A * | 5/2000 | Park | ............................ | 294/87.1 |
| 7,255,219 B2 * | 8/2007 | Rinke et al. | ................... | 198/458 |
| 7,540,369 B2 * | 6/2009 | Momich | ....................... | 198/418 |
| 2005/0126115 A1 | 6/2005 | Battisti | | |
| 2007/0137982 A1 | 6/2007 | Momich | | |

* cited by examiner

*Primary Examiner* — James R Bidwell
(74) *Attorney, Agent, or Firm* — Klaus J. Bach

(57) ABSTRACT

In an apparatus for separating parts arranged for example in at least two adjacent rows and including a transfer device, which is provided with at least two holding elements which pick up the parts in a first position and deposit them in a second position 5*b*, guide tracks are provided by which the distance at which the holding elements are disposed adjacent one another is changeable during the transport of the parts from the first position to the second position.

6 Claims, 4 Drawing Sheets

APPARATUS FOR SEPARATING PARTS

BACKGROUND OF THE INVENTION

The invention resides in an apparatus according to the preamble of claim 1 for separating for example parts arranged in at least two adjacent rows, including a transfer element having at least two retaining elements arranged side-by-side which engage parts in a first position and then deposit them in a second position.

Such apparatus are well-known in the art. They generally include an element which is rotatable about an axis and which is provided with several radially extending arms which are arranged side-by-side at a uniform angular distance from one another and which are provided at their ends with vacuum suction means. With the known apparatus, for example parts disposed on adjacently arranged transport belts can be grasped; pivoted by 90° or 180° and transferred to a downstream machine element.

The arms of the known separating apparatus are arranged firmly on a rotatable element in side-by-side relationship so that the distance at which they are arranged in side-by-side relationship cannot be changed. As a result, the parts can be deposited again only with the same sideward spacing relative to one another with which they were picked up. That is, with the known separating apparatus, the distance at which the parts are arranged side-by-side cannot be changed. This is disadvantageous in particular if the parts are arranged directly adjacent one another without any spacing, but it is necessary for the further treatment or handling of the parts that there is a space between adjacent sides of the parts.

It is the object of the present invention to provide an apparatus of the type described above which however allows the parts to be deposited at distances from each other which differ from the distances at which they were picked up by the apparatus.

SUMMARY OF THE INVENTION

In an apparatus for separating parts arranged in at least two rows extending side-by-side including a transfer element, which is provided with at least two holding elements for picking up the parts in a first position and depositing them in a second position, means are provided by which the distance at which the holding elements are arranged next to one another can be changed during the transport of the elements from the first position to the second position.

Since there are means by which the distance at which the holding elements are arranged adjacent to one another, can be changed during the transport of the parts from the first position to the second position the lateral distance between the parts, that is, the distance with which adjacent parts are disposed from one another can be changed in a simple manner. Since that distance is changed during the transport of the parts from the first position to the second position no separate operating step is required for the apparatus which is advantageous for the cycling time of the separating apparatus.

Advantageously, the means for changing the distance between the holding elements is in the form of longitudinal guide tracks with which the holding elements are operatively associated. In this way, the lateral distance between the holding elements can be changed during the transport of the parts from the first position to the second position in a simple manner. This can be achieved by an arrangement of the longitudinal guide tracks along the path from the first to the second position wherein they are arranged in the first position at a lateral distance as required for picking up the parts in the first position and, in the second portions they are arranged at a lateral distance as required for the holding elements to deposit the parts in the second position. The change-over of the distance occurs continuously.

The operative interaction between the holding elements and the longitudinal guide tracks can be established for example in that the holding elements include guide elements which are arranged in longitudinal grooves which are provided with the longitudinal guide tracks. However, rather than being arranged in the longitudinal groove, the guide elements may also be disposed between two guide tracks. In this way, the guide tracks do not need to be provided with longitudinal grooves which is advantageous regarding manufacturing costs. Furthermore, the area which would be occupied by the longitudinal tracks into which the longitudinal grooves would have to be cut, is available for the mounting of the longitudinal guide tracks. The change of the lateral distance between the holding elements can be avoided with the last mentioned embodiment by changing the width of the longitudinal guide tracks.

It is very advantageous if the holding elements are disposed in operative interaction with at least one transverse guide track as it is provided in another special embodiment of the invention. With the transverse guide track the lateral distance between the holding elements can be changed in a reliable manner. The holding elements may be attached for example to slide elements which are arranged in a correspondingly shaped groove of the transverse guide track. In this way, the holding elements are mounted in a reliably slideable manner.

Very advantageous is also an embodiment of the invention wherein the at least one transverse guide track extends rotatably around a vertical axis. That means the apparatus is cylindrical. This is advantageous because it reduces the space requirements for the apparatus.

With the transverse guide track being rotatable about a vertical axis, the longitudinal guide tracks must follow a correspondingly curved pattern. That is, the longitudinal guide tracks need to be annular. The holding elements then move along an annular track whereby the parts can be moved during the transport from the first position to the second position along a circular path for example by 180°. The parts may be picked up by the holding element for example in a vertical position on top and may be released in vertical position at the bottom.

In another particularly advantageous embodiment, several transverse guide tracks are provided which are adjustable for movement along the longitudinal guide tracks with different speeds. In this way, several parts disposed behind one another can be transported at the same time, which advantageously affects the cycle time of the apparatus.

In a four transverse guide track arrangement parts may for example be picked up and deposited by the holding elements at the same time, wherein during pick-up or respectively deposit of the parts, the transverse guide track by which the parts had been picked up, can be moved from the first to the second position and the transverse guide track, which had deposited the parts, can be moved from the second position to the first position. It is in this connection particularly advantageous that the holding elements can be adapted during pick up and during deposit of the parts, to the speed of the elements from which the parts are picked up or on which the parts are deposited. The elements can therefore be moved continuously. For pickup, the parts do not need to be spaced from one another.

In connection with the last-mentioned embodiment, it is particularly advantageous if the transverse guide track is mounted to hollow shafts which provides for a very compact apparatus design.

In a further special embodiment of the invention, the holding elements are connected to telescopic vacuum lines via which the holding elements can be evacuated. By way of the telescopic vacuum lines a vacuum can be generated at the holding elements in a simple and reliable manner. In this way, the parts can be rapidly and reliably and still carefully picked up by the holding elements.

In another particular embodiment of the invention, a reversing element is arranged in the area of the first position around which reversing element a carrier foil, on which the parts are arranged, can be redirected. With the use of a reversing element, the parts may be disposed on the carrier foil so as to adhere thereto. By reversing the carrier foil around the reversing element parts which are adhering to the carrier foil are released from the carrier foil and can then be reliably picked up by the holding elements.

It has been found to be very advantageous to arrange the separation apparatus according to the invention in a packaging machine by which the parts can be arranged between two foils. In particular, in a packaging machine in which for example so-called oral tabs (mouth care strips) are welded between two packaging foils the separating device according to the invention is very useful.

Further features and advantages of the present invention will become more readily apparent from the following description of particular exemplary embodiments thereof with reference to the accompanying drawings.

DESCRIPTION OF PARTICULAR EMBODIMENTS

Figure 1:
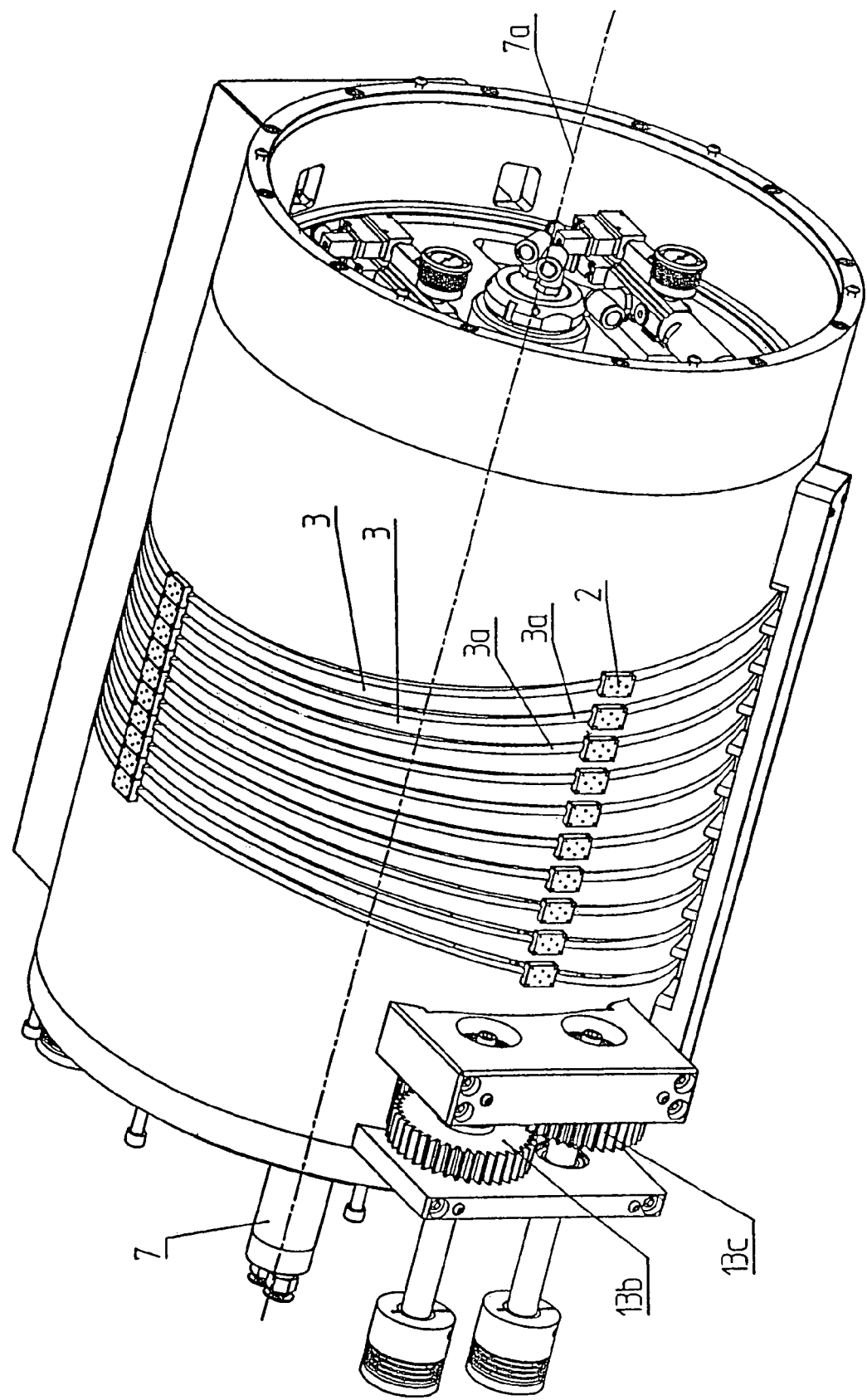
FIG. 1 is a schematic representation of a separating apparatus according to the invention in a perspective view.
Figure 2:
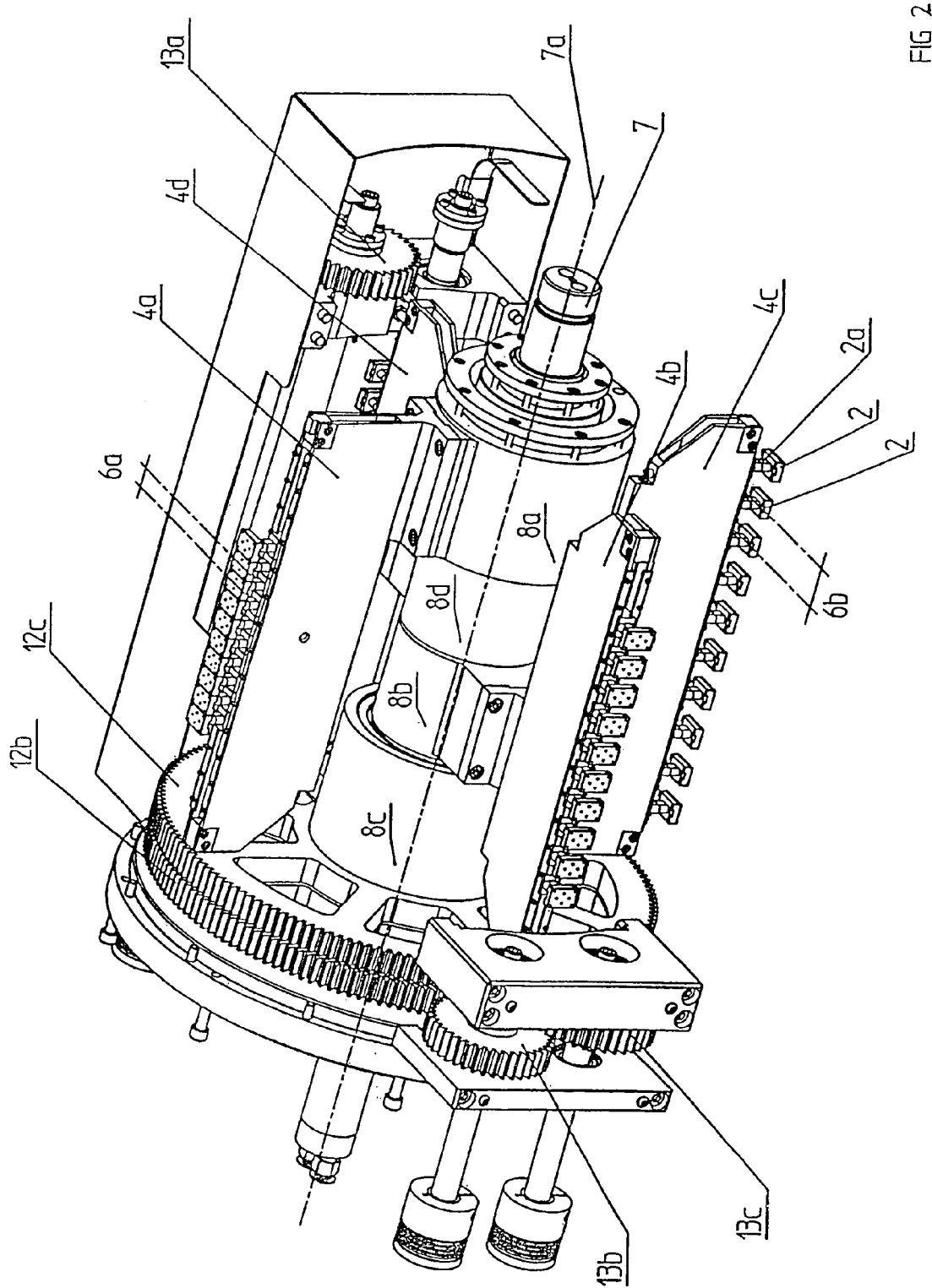
FIG. 2 shows the separating apparatus as shown in FIG. 1 but with several elements removed.
Figure 3:
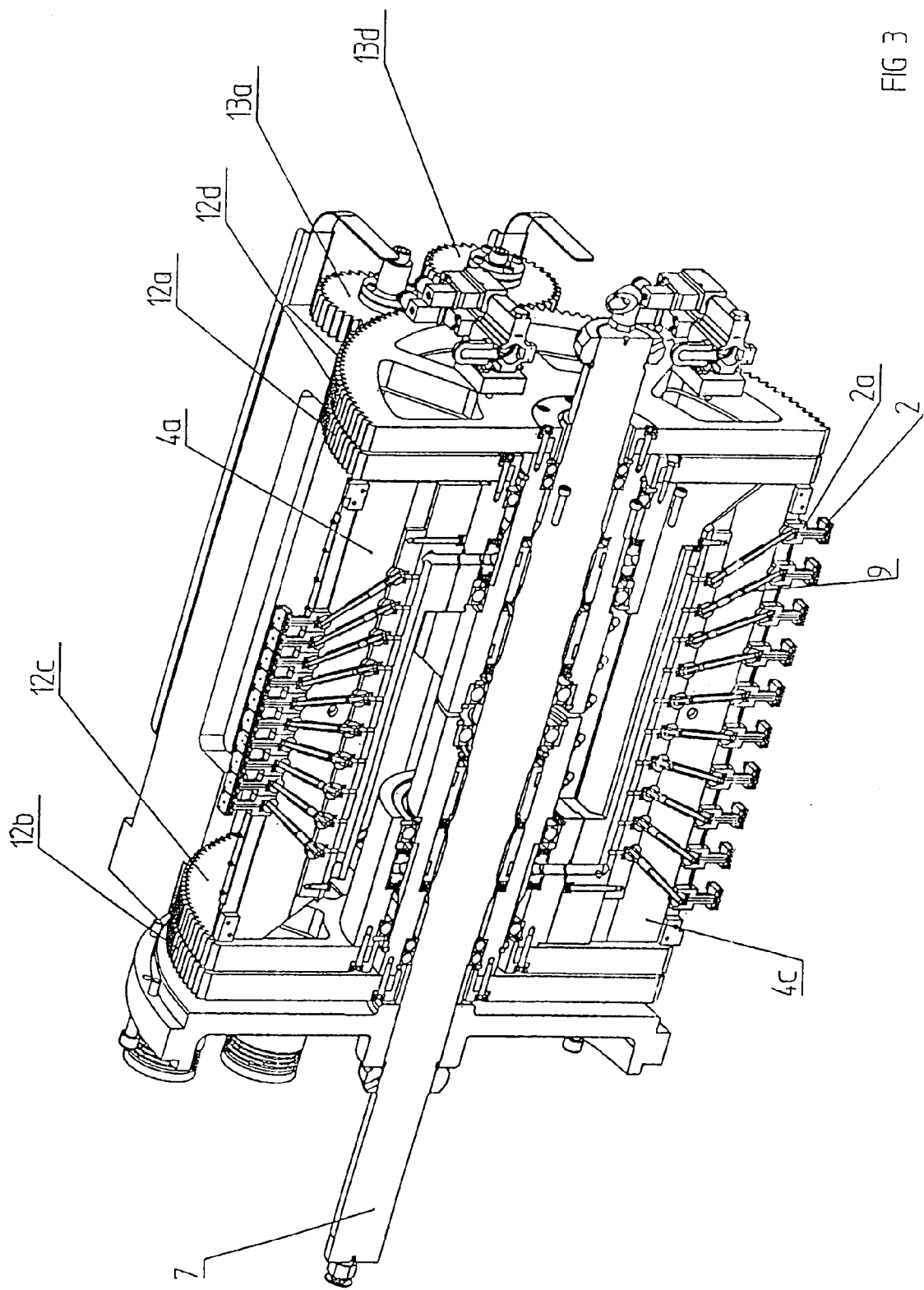
FIG. 3 shows the apparatus shown in FIG. 1 with further elements removed.

As apparent in particular from FIGS. 1 to 3, a separating apparatus according to the invention includes holding elements in the form of vacuum suction devices 2 wherein in the present case ten vacuum suction devices 2 are arranged next to one another. The vacuum suction devices 2 are arranged on carriages which are movably supported in a groove of a transverse guide track 4a to 4d and are in communication with the vacuum suction devices 2 via neck portions 2a. With the movable support of the vacuum suction devices 2 by the transverse guide tracks 4a to 4d, the lateral distance 6a, 6b at which the vacuum suction devices 2 are arranged next to one another, that is the distance 6a, 6b between the center lines of the vacuum suction devices 2, can be changed.

The transverse guide tracks 4a to 4d are each mounted to a hollow shaft 8a-8d, which is disposed on a drive shaft 7 that is rotatable about an imaginary axis 7a. The vacuum suction devices 2 are therefore movable along a circular path. Since each of the transverse guide tracks 4a to 4d is mounted to a separate hollow shaft 8a to 8d, the transverse guide tracks 4a-4d and, consequently, the vacuum suction devices 2 are arranged on one of the transverse tracks 4a to 4d can be adjusted independently of one another. For adjusting the hollow shafts 8a to 8d, the hollow shafts are provided with driven gear wheels 12a to 12d, which can be driven via drive gear wheels 13a to 13d, each by a separate drive which is not shown in the figures. In this way, the vacuum suction devices 2 can be adjusted to the speeds of parts 1 which are to be picked up by the suction devices 2. Also, the parts 1 attached to the vacuum suction devices 2 can be adjusted to the speed of a bottom foil 19 onto which the parts 1 are to be deposited. It is therefore not necessary to pick up the parts or deposit them in a discontinuous manner.

As apparent particularly from FIG. 1 longitudinal guide tracks 3 are arranged along the circular path along which the necks 2a of the vacuum suction devices are movable. The longitudinal guide tracks 3 are arranged at a distance from one another so that between two guide tracks 3, a slot 3a is formed. The width of the slot 3a corresponds about to the diameter of the necks 2a of the vacuum suction devices 2. The longitudinal guide tracks 3 and the vacuum suction devices 2 are so constructed or, respectively, arranged that the necks 2a of the vacuum suction devices 2 are disposed in the slots 3a.

The width of the longitudinal guide tracks 3 is not constant but changes continuously from a minimum width at the vertically upper part of the circular path to a maximum width at the vertically lowest part of the circular path. In this way, the distance between the slots 3a formed between two adjacent guide tracks 3 is continuously changed. Since the necks 2a of the vacuum suction devices 2 are disposed within the slots 3a also the distance between adjacent vacuum suction devices is continuously changed when the vacuum suction devices are moved along their circular paths, that is when the respective trans-verse guide track 4 is rotated about the imaginary axis 7a thereof.

The longitudinal guide tracks 3 are so designed that at the top of the circular path, the vacuum suction devices 2 are arranged in side-by-side relationship essentially without any distance from one another, or, respectively, that the center lines of the vacuum suction devices 2 are disposed at a first distance 6a from one another. When displaced by 180° that is when at the bottom of the circular path, the vacuum devices 2 have a distance from one another which is determined by the distance at which the parts 1 held by the vacuum suction devices 2 are to be deposited. That is, in this position, the center lines of the vacuum suction devices have a second distance 6b from one another.

For picking up the parts, a vacuum is applied to the vacuum suction devices 2. To this end, the vacuum suction devices are in communication, via telescopic vacuum ducts 9, with a channel in which a vacuum can be generated. This is shown specifically in FIG. 3.

Figure 4:
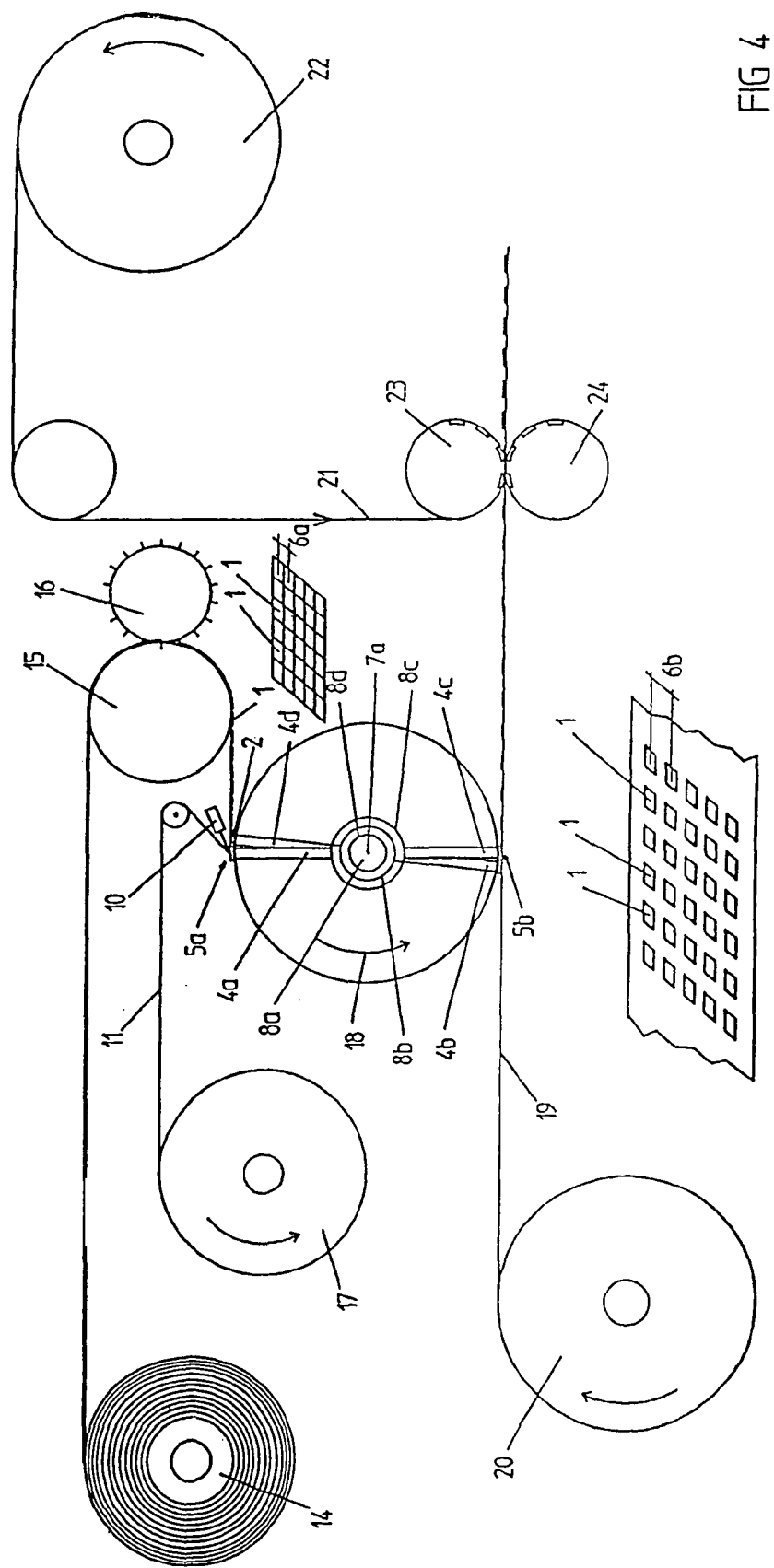
FIG. 4 is a schematic representation of a packaging machine including the separating apparatus according to the invention.

Below, the functioning of the separating apparatus according to the invention will be described in connection with a packaging machine as shown in FIG. 4.

As shown in FIG. 4, a carrier foil strip 11 is wound onto a product spool 14 to which a carrier strip is attached, at one side of which a film consisting of an effective substance is provided. The carrier foil strip 11, together with the effective substance, is advanced through a pair of cutting rollers 15, 16 by which the effective material film is sectioned into rectangular parts 1. After passage through the roller pair 15, 16 consequently individual rectangular parts 1 of the effective substance film are disposed on the carrier foil strip 11. The parts 1 are separated only by a cutting gap so that, in principle, they abut one another.

After passage through the cutting roller pair 15, 16, the carrier foil 11 is guided around a wedge-shaped redirecting element 10 whereby the parts 1 of the effective substance which are attached to the carrier foil are released therefrom.

Below the wedge-shaped element 10, a separating apparatus according to the present invention is arranged wherein the wedge-shaped element 10 or respectively the separating apparatus are so arranged that a part 1 after being released from the carrier foil 11 while the carrier foil is being redirected is instantly picked up by a vacuum suction device 2. To this end, the respective vacuum suction devices 2, or, respectively, the respective first traverse guide track 4a needs to be in a first position 5a. With a continuous movement of the carrier foil, the respective hollow shaft 8a of the respective transverse guide track 4a is operated by the drive thereof at such a speed that the respective vacuum suction devices 2 advance at the same speed as the carrier foil 11. After its reversing around the wedge element 10, the carrier foil 10 is wound onto a foil spool 17.

The separating apparatus includes four transverse guide tracks 4a to 4d. The number of vacuum suction devices 2 arranged on each of the transverse guide tracks 4a to 4d corresponds to the number of parts 1 disposed on the carrier foil 11 laterally next to one another. As a result, all of the parts 1 arranged on a carrier foil 11 laterally adjacent one another can be picked up at the same time.

FIG. 4 shows the first transverse guide track 4a in a position in which the vacuum suction devices 2 disposed thereon are in their first position 5a. After the parts 1 have been picked up by the respective vacuum suction devices 2, the respective transverse guide track 4a is advanced in the direction of the arrow 18 at high speed until the vacuum suction devices 2 are disposed just ahead of the second position 5b. In FIG. 4, the second guide track 4b is shown in this position. In the second position, in which in FIG. 4 the third transverse guide track 4c is shown, the parts 1 are deposited onto the bottom foil 19, which has been mentioned earlier and which is unwound from a bottom foil spool 20.

While the vacuum suction devices 2 arranged at the first transverse guide track 4 pick up parts 1 from the carrier foil 11, the vacuum suction device 2 of the third transverse guide track 4c, which is already at the second position 5b, deposits parts 1 on the bottom foil 19.

Since the parts 1 are deposited on the bottom foil 19 in spaced relationship, the bottom foil 19 is moved along at a higher speed than the carrier foil 11. With a continuous movement of the bottom foil 19, the respective hollow shaft 8c of the third transverse guide track 4c is driven by its drive at such a speed that the respective vacuum suction devices 2 move at the same speed as the bottom foil 19.

When all the parts 1 have been deposited from the respective vacuum suction devices 2 onto the bottom foil 19, the respective transfer guide track 4c is moved at high speed in the direction of the arrow 18 until the vacuum suction devices 2 arranged thereon are disposed shortly ahead of the first position 5a in which the parts 1 are picked up by the respective vacuum suction devices 2 from the carrier foil 11. In FIG. 4, the forth transverse guide track 4d is shown in this position.

Since the necks 2a of the vacuum suction device 2 are accommodated in the slots 3a and the distance between the slots 3a with respect to one another changes from the first position 5a to the second position 5b, along the path of the vacuum suction devices 2 from the first positions 5a to the second position 5b also the distance with which the respective vacuum suction devices 2 are disposed next to one another, or, respectively the distance 6a, 6b between the center lines of the respective vacuum suction devices 2 changes. The parts 1 therefore are arranged in the second position 5b at a lateral distance 6b from one another which is larger than their lateral distance in the first position 5a. The lateral distance in the second position 5b corresponds to the distance with which the parts 1 are deposited on the bottom foil 19.

In the same way, in which the distances between the vacuum suction devices are changed on the way from the first position 5a to the second position 5b, the lateral distance of the vacuum suction devices 2 relative to one another is changed on the way from the second position 5b to the first position 5a. That is, after the vacuum suction device 2 has been moved from the second position 5b to the first position 5a, their center lines are no longer at the second distance 6b which they had in the second position 5b but at the lesser first distance 6a which means that the vacuum suction device are arranged again directly adjacent one another.

When the parts 1 have been deposited on the bottom foil 19, a cover foil 21 which is unwound from a cover foil spool 22, is placed onto the bottom foil 19 as well as the parts 1 to cover the parts on the bottom foil. After placement of the cover foil 21 onto the bottom foil 19, the arrangement comprising the bottom foil 19, the parts 1 and the cover foil 21 passes through a seal roller pair 23, 24 by which the cover foil 21 is welded to the bottom foil.

What is claimed is:

1. An apparatus for separating parts (1) arranged in at least two rows disposed next to one another, including:
   a transfer device (2, 4) with at least two holding elements (2) which are disposed adjacent one another and which are capable of picking up parts (1) in a first position (5a) and depositing them in a second position (5b), the holding elements (2) being operatively associated with several transverse guide tracks (4a to 4d), which are arranged so as to be rotatable about an imaginary axis (7a), the transverse guide tracks (4a-4d) being controllably movable along the longitudinal guide track (3) and
   means (3, 4) by which the distance (6a, 6b) at which the holding elements (2) are disposed adjacent one another is changeable during the transport of the parts (1) from the first position (5a) to the second position (5b).

2. The apparatus according to claim 1, wherein the means (3,) for changing the distance (6a, 6b) of the holding elements (2) is in the form of longitudinal guide tracks (3) with which the holding elements (2) are operatively associated.

3. The apparatus according to claim 1, wherein the transverse guide tracks (4a to 4d) are mounted on hollow shafts (8a to 8d).

4. The apparatus according to claim 1, wherein the holding elements (2) are connected to telescopic vacuum suction lines (9) by way of which a vacuum can be applied to the holding elements (2).

5. The apparatus according to claim 1, wherein, in the area of the first position (5a, a reversing element(10) is arranged around which a carrier foil (11), on which the parts (1) are disposed, can be redirected.

6. Packaging machine including an apparatus for separating parts (1) arranged in at least two rows disposed next to one another, said apparatus including:
   a transfer device (2, 4) with at least two holding elements (2) which are disposed adjacent one another and which are capable of picking up parts (1) in a first position (5a) and depositing them in a second position (5b), the holding elements (2) being operatively associated with several transverse guide tracks (4a to 4d), which are arranged so as to be rotatable about an imaginary axis (7a), the transverse guide tracks (4a-4d) being controllably movable along the longitudinal guide tracks (3), and
   means (3, 4) by which the distance (6a, 6b) at which the holding elements (2) are disposed adjacent one another is changeable during the transport of the parts (1) from the first position (5a) to the second position (5b).

* * * * *